United States Patent
Weitz et al.

(10) Patent No.: US 12,271,431 B1
(45) Date of Patent: Apr. 8, 2025

(54) SYSTEM AND METHOD FOR CONTENT SHARING IN ENTERPRISE CONTENT MANAGEMENT

(71) Applicant: Veeva Systems Inc., Pleasanton, CA (US)

(72) Inventors: Leah Avalon Weitz, Portland, OR (US); Stephen Paul Harper, Moraga, CA (US); Bailey Chen, Palo Alto, CA (US); Joshua Andrew Lim, Pleasanton, CA (US); Sindhusha Reddy Jensen, San Ramon, CA (US); Eric Bezar, Berkeley, CA (US); Jon Stone, Olympia, WA (US); Derek Allwardt, Pleasanton, CA (US); Richard Mayfield, Pleasanton, CA (US)

(73) Assignee: Veeva Systems Inc., Pleasanton, CA (US)

( * ) Notice: Subject to any disclaimer, the term of this patent is extended or adjusted under 35 U.S.C. 154(b) by 869 days.

(21) Appl. No.: 17/162,487

(22) Filed: Jan. 29, 2021

(51) Int. Cl.
| | |
|---|---|
| *G06F 16/00* | (2019.01) |
| *G06F 16/176* | (2019.01) |
| *G06F 16/907* | (2019.01) |
| *G06F 16/93* | (2019.01) |
| *G16H 10/20* | (2018.01) |

(52) U.S. Cl.
CPC ............ *G06F 16/94* (2019.01); *G06F 16/176* (2019.01); *G06F 16/907* (2019.01); *G16H 10/20* (2018.01)

(58) Field of Classification Search
CPC ...... G06F 16/94; G06F 16/907; G06F 16/176; G16H 10/20
USPC ........................................................... 707/626
See application file for complete search history.

(56) References Cited

U.S. PATENT DOCUMENTS

| | | | |
|---|---|---|---|
| 6,151,606 A | 11/2000 | Mendez | |
| 7,143,103 B1 | 11/2006 | Zisman et al. | |
| 7,844,890 B2 | 11/2010 | Schmidt | |
| 8,244,713 B2 | 8/2012 | Petri | |
| 8,504,519 B1 | 8/2013 | Sachs et al. | |
| 8,566,338 B2 | 10/2013 | Cragun et al. | |
| 8,583,614 B1 | 11/2013 | Dilts et al. | |
| 8,694,535 B2 * | 4/2014 | Oleynik | G06F 16/35 707/769 |
| 10,032,133 B2 | 7/2018 | Follis | |
| 10,204,088 B2 | 2/2019 | Bezar et al. | |
| 10,795,961 B2 * | 10/2020 | Welch | G06F 16/9566 |
| 11,087,082 B1 | 8/2021 | Bezar et al. | |
| 11,256,395 B2 * | 2/2022 | Sterin | G06F 16/93 |
| 2006/0015879 A1 | 1/2006 | Wu et al. | |
| 2007/0150433 A1 | 6/2007 | Chen | |

(Continued)

*Primary Examiner* — Tyler J Torgrimson

(57) ABSTRACT

Systems and methods for re-using content in a content management system. The content management system may have two or more repositories. A link document may be generated in a link repository for a source document in a source repository. The link document may be a copy of the source document, and synchronized to the source document in a number of different ways, dynamically or statically. When the source document is updated, the source repository may notify the link repository about the change, receive a pull request from the link repository for the change, and generate an updated link document. A static copy of the link document may be created to prevent further changes to the link document for business or compliance purposes.

17 Claims, 18 Drawing Sheets

(56) References Cited

U.S. PATENT DOCUMENTS

| | | |
|---|---|---|
| 2008/0168106 A1 | 7/2008 | Freedman |
| 2008/0201349 A1 | 8/2008 | Petri |
| 2009/0031251 A1 | 1/2009 | Kessler et al. |
| 2009/0125571 A1 | 5/2009 | Kiilerich et al. |
| 2009/0287746 A1 | 11/2009 | Brown |
| 2010/0241940 A1 | 9/2010 | Rao et al. |
| 2011/0239231 A1 | 9/2011 | Brown et al. |
| 2011/0276897 A1* | 11/2011 | Crevier ............... H04L 61/4555 |
| | | 715/752 |
| 2012/0030247 A1 | 2/2012 | Yambal et al. |
| 2013/0117289 A1 | 5/2013 | Fischer et al. |
| 2013/0254897 A1 | 9/2013 | Reedy et al. |
| 2014/0006352 A1 | 1/2014 | Sachs et al. |
| 2014/0040714 A1 | 2/2014 | Siegel et al. |
| 2014/0237342 A1* | 8/2014 | King ..................... G06F 16/955 |
| | | 715/224 |
| 2014/0372956 A1 | 12/2014 | Bisca et al. |
| 2015/0012861 A1 | 1/2015 | Loginov |
| 2015/0134629 A1 | 5/2015 | Knobloch et al. |
| 2015/0261792 A1* | 9/2015 | Attarde ................ G06F 16/215 |
| | | 707/616 |
| 2016/0188584 A1* | 6/2016 | Glover ................. G06F 16/285 |
| | | 707/608 |
| 2016/0224548 A1 | 8/2016 | Massand |
| 2016/0314102 A1* | 10/2016 | Bezar .................... G06F 40/197 |
| 2017/0099347 A1* | 4/2017 | Pucha ................... H04L 63/101 |
| 2018/0276270 A1* | 9/2018 | Bisbee ............... G06Q 30/0241 |

\* cited by examiner

SYSTEM AND METHOD FOR CONTENT SHARING IN ENTERPRISE CONTENT MANAGEMENT

CROSS-REFERENCE TO RELATED APPLICATIONS

The present application relates U.S. patent application Ser. No. 14/695,703, filed on Apr. 24, 2015, issued as U.S. Pat. No. 10,204,088, and entitled "System and Method for Content Sharing in Enterprise Content Management," which is hereby incorporated by reference herein for all purposes.

BACKGROUND

The subject technology relates generally to content management, and more particularly to sharing content among repositories in enterprise content management.

Users increasingly depend on content management systems because of their ubiquitous and managed access, from anywhere, at any time, from any device. However, previous content management systems do not support content sharing across repositories. To use content from one repository in another repository, some users manually transfer content between the repositories which requires downloading and uploading content and is inconvenient and time consuming, while other users store all content in a single consolidated repository which is inflexible and hard to maintain.

Thus, it is desirable to enable content sharing among repositories in enterprise content management to support seamless cross-repository business processes and allow users to interact, in their specific business context, with content from different repositories.

SUMMARY

The disclosed subject matter relates to a method for re-using content in a content management system which has a first repository and a second repository. The method comprises: storing a source document in the first repository; determining if a request for generating a link document in the second repository is received; displaying a user interface ("UI") for selecting a source document when a request for generating the link document is received; displaying a UI for generating the link document; receiving metadata for the link document on the UI for generating the link document; and generating the link document in the second repository. The metadata for the link document comprises a first field for indicating a type of synchronization between the link document and the source document. The link document is a copy of the source document and is synchronized to the source document. The method further comprises receiving a first predetermined requirement for creating a static copy of the link document, wherein no change is permitted to be made to the static copy of the link document.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, well-known structures and components are shown in block diagram form in order to avoid obscuring the concepts of the subject technology.

The subject technology is directed to techniques for sharing or re-using content across repositories in enterprise content management. The content management system may have two or more repositories. Each repository may be associated with a front-end application which has a specific business context, and store a specific category of content generated in the specific business context. When a user wants to use a source document in a first repository with a second front-end application associated with a second repository, instead of downloading the source document from the first repository and then uploading it to the second repository, the user may create a link document in the second repository. The link document may be a copy of the source document, and synchronized to the source document in a number of different ways, dynamically or statically. When the source document is updated, a notification about the update may be sent from the first repository to the second repository, so that the link document may be updated according to the type of synchronization between the source document and the link document.

Figure 1:
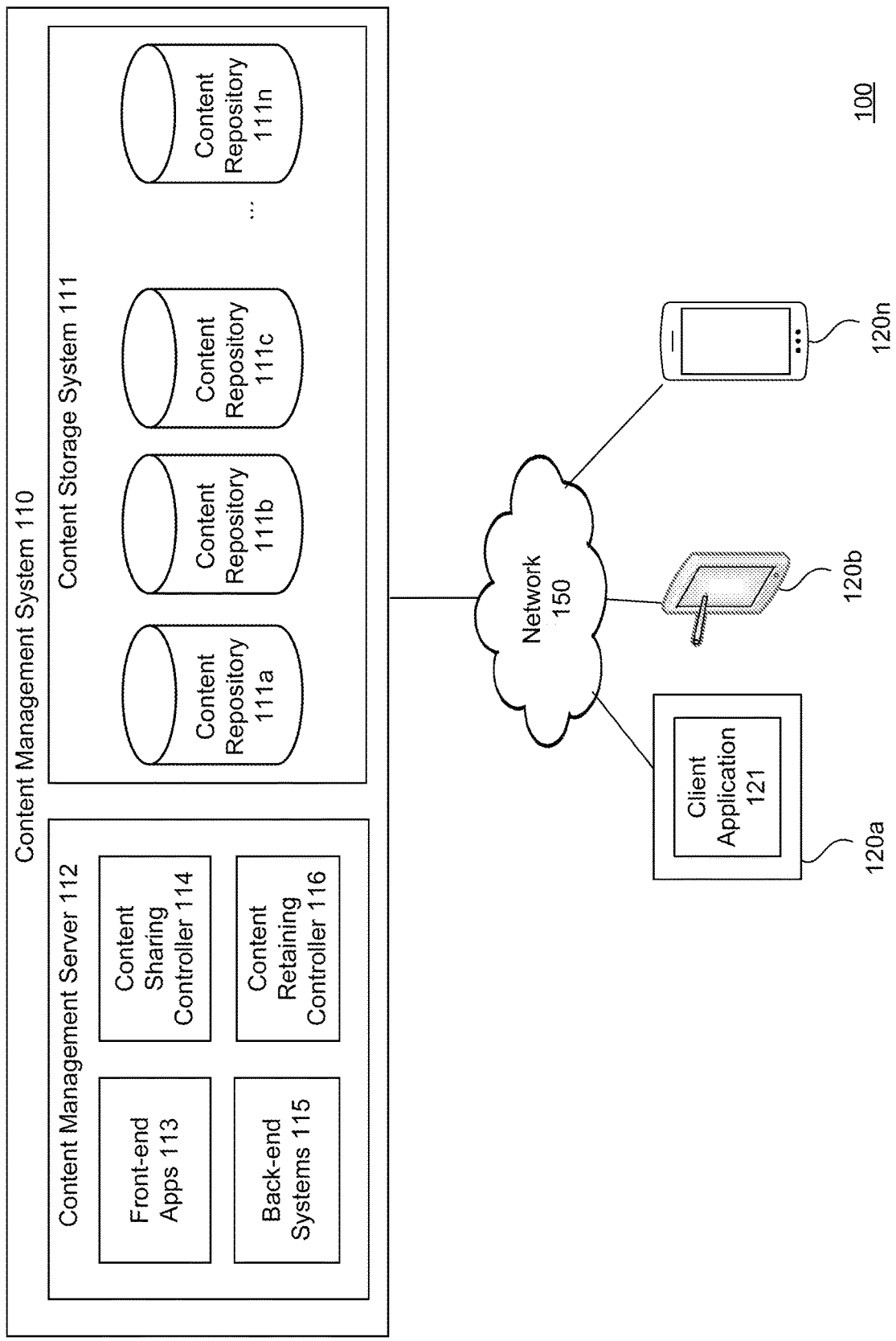
FIG. 1 illustrates an example high level block diagram of an enterprise content management architecture wherein the present invention may be implemented.

FIG. 1 illustrates an example high level block diagram of an enterprise content management architecture 100 wherein the present invention may be implemented. The enterprise may be a business, or an organization. As shown, the architecture 100 may include a content management system 110, and a plurality of user computing devices 120a, 120b, ... 120n, coupled to each other via a network 150. The content management system 110 may include a content storage system 111 and a content management server 112. The content storage system 111 may have two or more content repositories, e.g., 111a, 111b, 111c ... and 111n. The network 150 may include one or more types of communication networks, e.g., a local area network ("LAN"), a wide area network ("WAN"), an intra-network, an inter-network (e.g., the Internet), a telecommunication network, and peer-to-peer networks (e.g., ad hoc peer-to-peer networks), which may be wired or wireless.

The user computing devices 120a-120n may be any machine or system that is used by a user to access the content management system 110 via the network 150, and may be any commercially available computing devices including laptop computers, desktop computers, mobile phones, smart phones, tablet computers, netbooks, and personal digital assistants (PDAs). A client application 121 may run from a user computing device, e.g., 120a, and access content in the content management system 110 via the network 150. User computing devices 120a-120n are illustrated in more detail in FIG. 4.

The content storage system 111 may store content that client applications (e.g., 121) in user computing devices 120a-120n may access and may be any commercially available storage devices. As will be described with reference to FIG. 2 below, each content repository (e.g., 111a, 111b, 111c or 111n) may store a specific category of content, be the source repository for its content, and allow users to interact with its content in a specific business context. The content in a first repository (e.g., 111a) may be re-used in a second repository (e.g., 111b or 111c), and users may be allowed to interact with content from the first repository in the specific business context for the second repository. One content repository (e.g., 111a) may be a source repository for one document, but a link repository for another document. A source document may be re-used in multiple link repositories.

The content management server 112 is typically a remote computer system accessible over a remote or local network, such as the network 150. The content management server 112 could be any commercially available computing devices. A client application (e.g., 121) process may be active on one or more user computing devices 120a-120n. The corresponding server process may be active on the content management server 112, as one of the front-end applications 113 described with reference to FIG. 2. The client application process and the corresponding server process may communicate with each other over the network 150, thus providing distributed functionality and allowing multiple client applications to take advantage of the information-gathering capabilities of the content management system 110.

In one implementation, the content management server 112 may include a content sharing controller 114 which may control the process for generating a link document and the process for synchronizing a source document and its link documents, as will be described with reference to FIG. 11 below.

Figure 12:
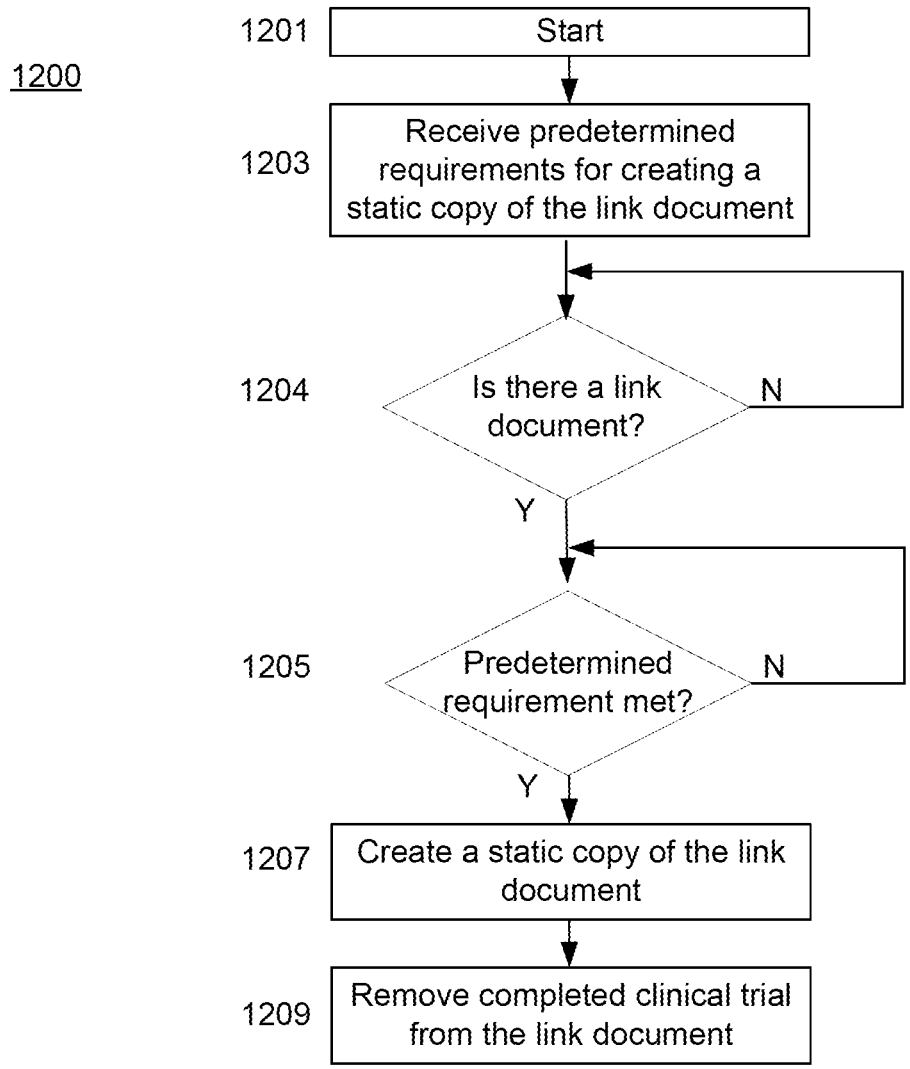
FIG. 12 illustrates a flowchart of a method for retaining a static copy of a link document in an enterprise content management system according to one embodiment of the present invention.

In one implementation, the content management server 112 may include a content retaining controller 116 which may control the process for generating a database copy of a link document, as will be described with reference to FIG. 12 below.

Although the front-end applications 113, the back-end systems 115 and the content sharing controller 114 are shown in one server, it should be understood that they may be implemented in multiple computing devices.

In one implementation, the content management system 110 may be a multi-tenant system where various elements of hardware and software may be shared by one or more customers. For instance, a server may simultaneously process requests from a plurality of customers, and the content storage system 111 may store content for a plurality of customers. In a multi-tenant system, a user is typically associated with a particular customer. In one example, a user could be an employee of one of a number of pharmaceutical companies which are tenants, or customers, of the content management system 110.

In one embodiment, the content management system 110 may run on a cloud computing platform. Users can access content on the cloud independently by using a virtual machine image, or purchasing access to a service maintained by a cloud database provider.

In one embodiment, the content management system 110 may be provided as Software as a Service ("SaaS") to allow users to access the content management system 110 with a thin client.

Figure 2:
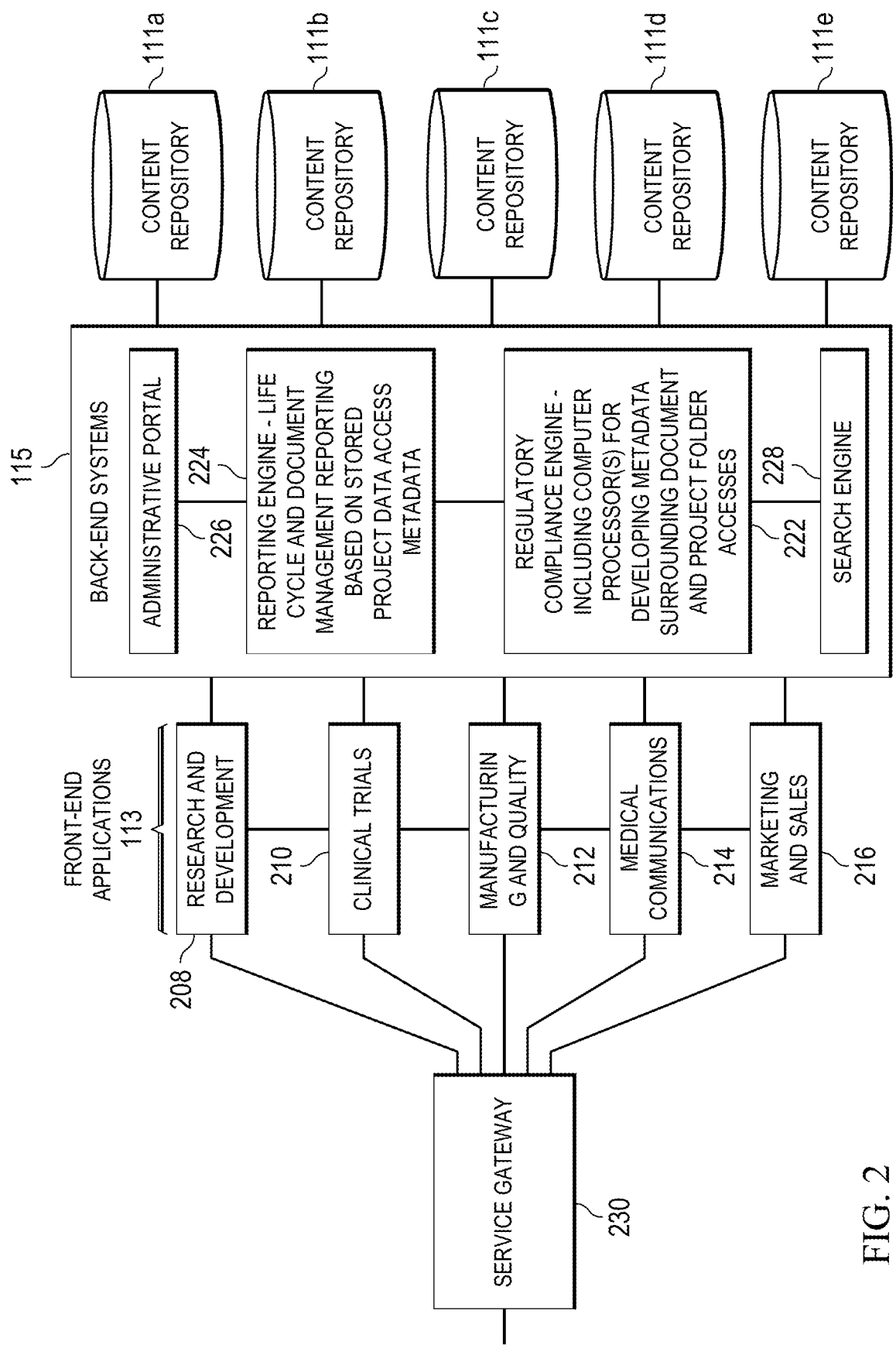
FIG. 2 provides a description of the content management system with additional specific applications and interfaces connected thereto.

FIG. 2 provides a description of the content storage system 111 with additional specific applications and interfaces connected thereto. In an embodiment, this content storage system 111 is a cloud-based or distributed network based system for consolidating an enterprise's data, oftentimes integrating multiple content repositories in an enterprise into a single system having coordinated control, measuring, and auditing of data creation, access and distribution.

In an embodiment of the content storage system 111 for the life sciences industry, as illustrated in the figure, this content storage system 111 can include specific data collections for the following areas and/or business process-specific front-end applications 113:

The Research & Development (R&D) front-end application 208 provides for an aggregation of materials in support of research and initial clinical trial submissions through building organized and controlled content repositories within the content management system 110, more specifically, the content repository 111a. Elements that can be stored, organized, and managed through this front-end include submission bills of materials, Drug Information Association (DIA) reference models support, and submission-ready renderings. This front-end 208 is designed to provide an interface to the content management system 110 whereby researchers, contract research organizations (CROs), and other collaboration partners can access and/or distribute content through a single controlled document system.

The clinical trials front-end application 210 provides for faster and more organized access to trial documents and reports, while supporting seamless collaboration between sponsors, CROs, sites, investigators and other trial participants. Specific features both ease study and site administration as well as support the DIA trial master file (TMF) reference model. Having this front-end application providing access to the content management system 110 further provides for efficient passing off of content, e.g., in the content repository 111b, between this phase and other phases of the life sciences development process.

The manufacturing and quality application 212 enables the creation, review, approval and distribution of controlled documents across the organization and with external partners in the context of materials control and other manufacturing elements. The application 212 provides functionality in support of the manufacturing process including watermarking, controlled print, signature manifestation and "Read and Understood" signature capabilities. The documents and metadata associated with this process is managed and stored in the content management system 110, or more specifically, the content repository 111*c*, whereby it can be assured that the related documents are not distributed in contravention of law and company policy.

The medical communications application 214 provides for communications with medical facilities, including call center access, integration, and interface functionality. Particular access control features and metadata associated with this application 214 include expiration and periodic review elements, multi-channel support, global documents and automatic response package generation through the content management system 110. Related documents may be stored in the content repository 111*d*.

The marketing and sales application 216 provides an end-to-end solution for the development, approval, distribution, expiration and withdrawal of promotional materials. Specific features include support for global pieces, approved Form FDA 2253 (or similar international forms) form generation, online document, and video annotation, and a built-in digital asset library (DAL). Again, the communications may be through the content management system 110, and the promotional materials may be stored in the content repository 111*e*.

In disclosed embodiments, there are provided a number of back-end system applications 115 that provide for the management of the data, forms, and other communications in the content management system 110. For example, the back-end systems applications 115 may include a regulatory compliance engine 222 to facilitate regulatory compliance, including audit trail systems, electronic signatures systems, and system traceability to comply with government regulations, such as 21 CFR Part 11, Annex 11 and GxP-related requirements. The regulatory compliance engine 222 may include processors for developing metadata surrounding document and project folder accesses so from a regulatory compliance standpoint it can be assured that only allowed accesses have been permitted. The regulatory compliance engine 222 may further includes prevalidation functionality to build controlled content in support of installation qualification (IQ) and/or operational qualification (OQ), resulting in significant savings to customers for their system validation costs.

In further disclosed embodiments, the back-end systems 115 may contain a reporting engine 224 that reports on documents, their properties and the complete audit trail of changes. These simple-to-navigate reports show end users and management how content moves through its life cycle over time, enabling the ability to track 'plan versus actual' and identify process bottlenecks. The reporting engine may include processors for developing and reporting life cycle and document management reporting based on stored project data and access metadata relative to documents, forms and other communications stored in the content management system 110.

In further disclosed embodiments, the back-end systems 115 can include an administrative portal 226 whereby administrators can control documents, properties, users, security, workflow and reporting with a simple, point-and-click web interface. Customers also have the ability to quickly change and extend the applications or create brand new applications, including without writing additional software code.

In further disclosed embodiments, the back-end systems 115 may include a search engine 228 whereby the content management system 110 can deliver simple, relevant and secure searching.

The content management system 110 may have more back-end systems.

In providing this holistic combination of front-end applications 113 and back-end systems 115, the various applications can further be coordinated and communicated with by the service gateway 230, which in turn can provide for communications with various web servers and/or web services APIs. Such web servers and/or web services APIs can include access to the content and metadata layers of some or all of the various front-end applications 113 and back end systems 115, enabling seamless integration among complementary systems.

In the context of the described embodiments, content in one repository, e.g., the content repository 111*a* for the Research & Development (R&D) front-end application 208, may be re-used in another repository (e.g., the content repository 111*d*) with another front-end application (e.g., the medical communications application 214).

The content management system 110 may store content for other industries.

Figure 3:
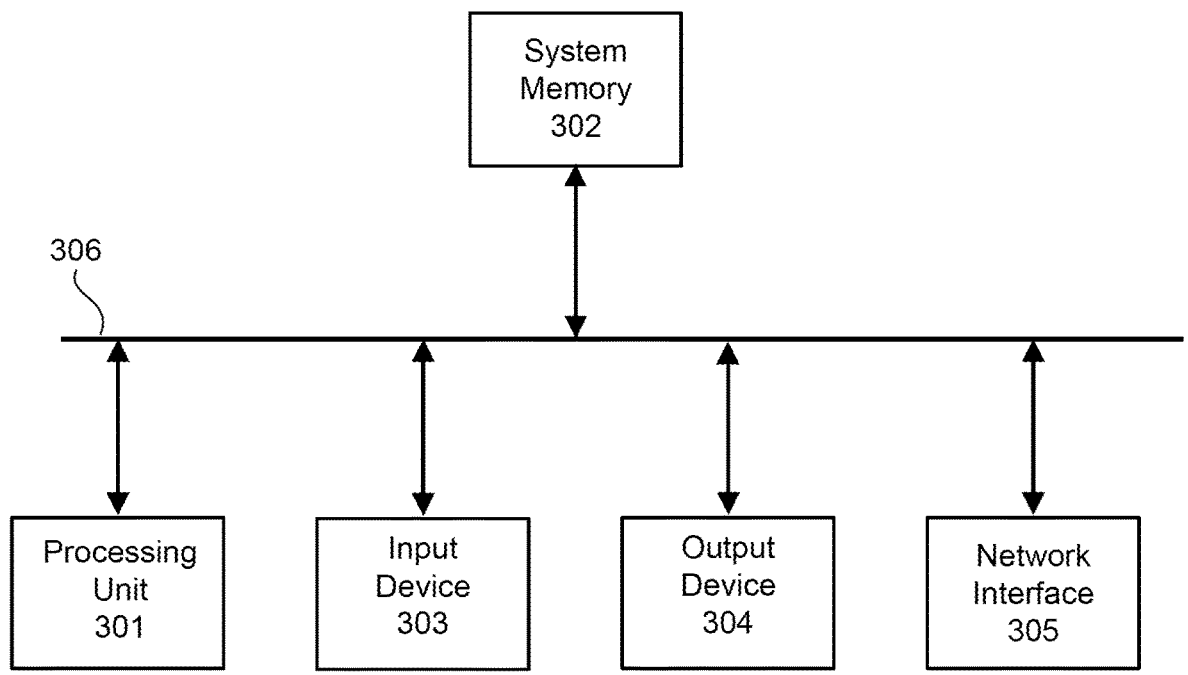
FIG. 3 illustrates an example block diagram of a computing device.

FIG. 3 illustrates an example block diagram of a computing device 300 which can be used as the user computing devices 120*a*-120*n*, and the content management server 112 in FIG. 1. The computing device 300 is only one example of a suitable computing environment and is not intended to suggest any limitation as to scope of use or functionality. The computing device 300 may include a processing unit 301, a system memory 302, an input device 303, an output device 304, a network interface 305 and a system bus 306 that couples these components to each other.

The processing unit 301 may be configured to execute computer instructions that are stored in a computer-readable medium, for example, the system memory 302. The processing unit 301 may be a central processing unit (CPU).

The system memory 302 typically includes a variety of computer readable media which may be any available media accessible by the processing unit 301. For instance, the system memory 302 may include computer storage media in the form of volatile and/or nonvolatile memory such as read only memory (ROM) and/or random access memory (RAM). By way of example, but not limitation, the system memory 302 may store instructions and data, e.g., an operating system, program modules, various application programs, and program data.

A user can enter commands and information to the computing device 300 through the input device 303. The input device 303 may be, e.g., a keyboard, a touchscreen input device, a touch pad, a mouse, a microphone, and/or a pen.

The computing device 300 may provide its output via the output device 304 which may be, e.g., a monitor or other type of display device, a speaker, or a printer.

The computing device 300, through the network interface 305, may operate in a networked or distributed environment using logical connections to one or more other computing devices, which may be a personal computer, a server, a router, a network PC, a peer device, a smart phone, or any other media consumption or transmission device, and may include any or all of the elements described above. The logical connections may include a network (e.g., the network 150) and/or buses. The network interface 305 may be configured to allow the computing device 300 to transmit and receive data in a network, for example, the network 150. The network interface 305 may include one or more network interface cards (NICs).

Figure 4:
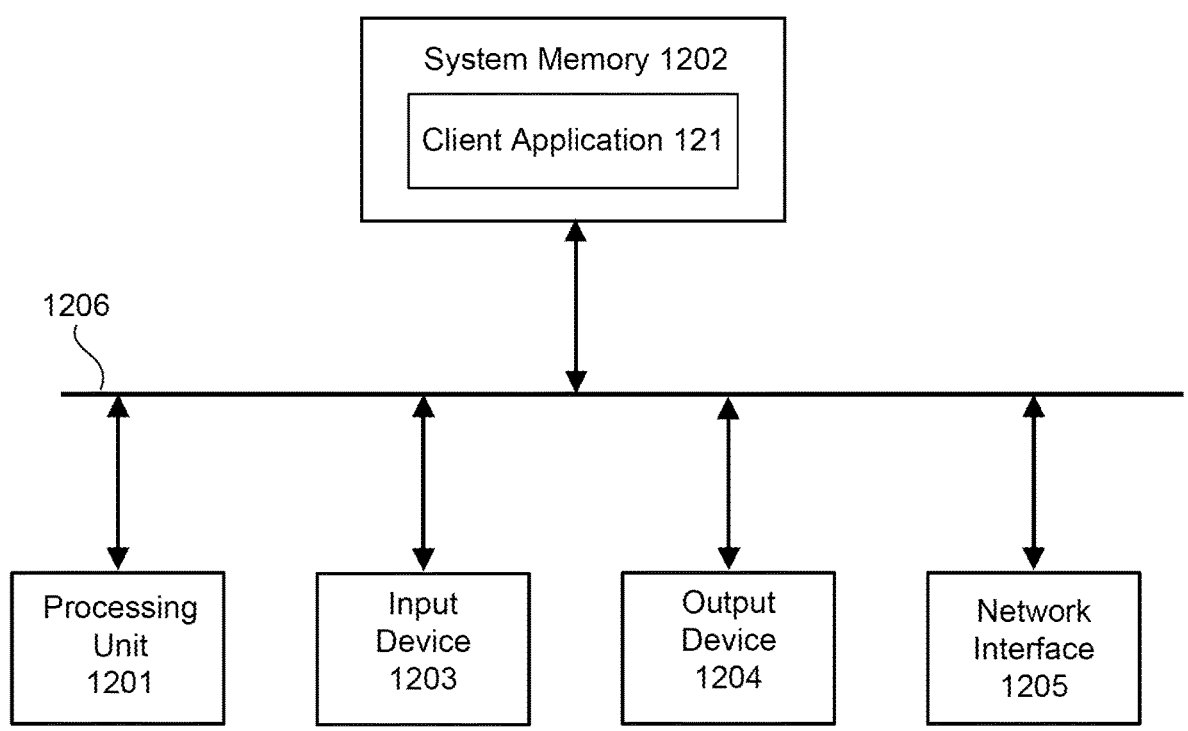
FIG. 4 illustrates an example high level block diagram of a user computing device.

FIG. 4 illustrates an example high level block diagram of a user computing device (e.g., 120*a*) wherein the present invention may be implemented. The user computing device 120*a* may be implemented by the computing device 300 described above, and may have a processing unit 1201, a system memory 1202, an input device 1203, an output device 1204, and a network interface 1205, coupled to each other via a system bus 1206. The system memory 1202 may store the client application 121.

Figure 5:
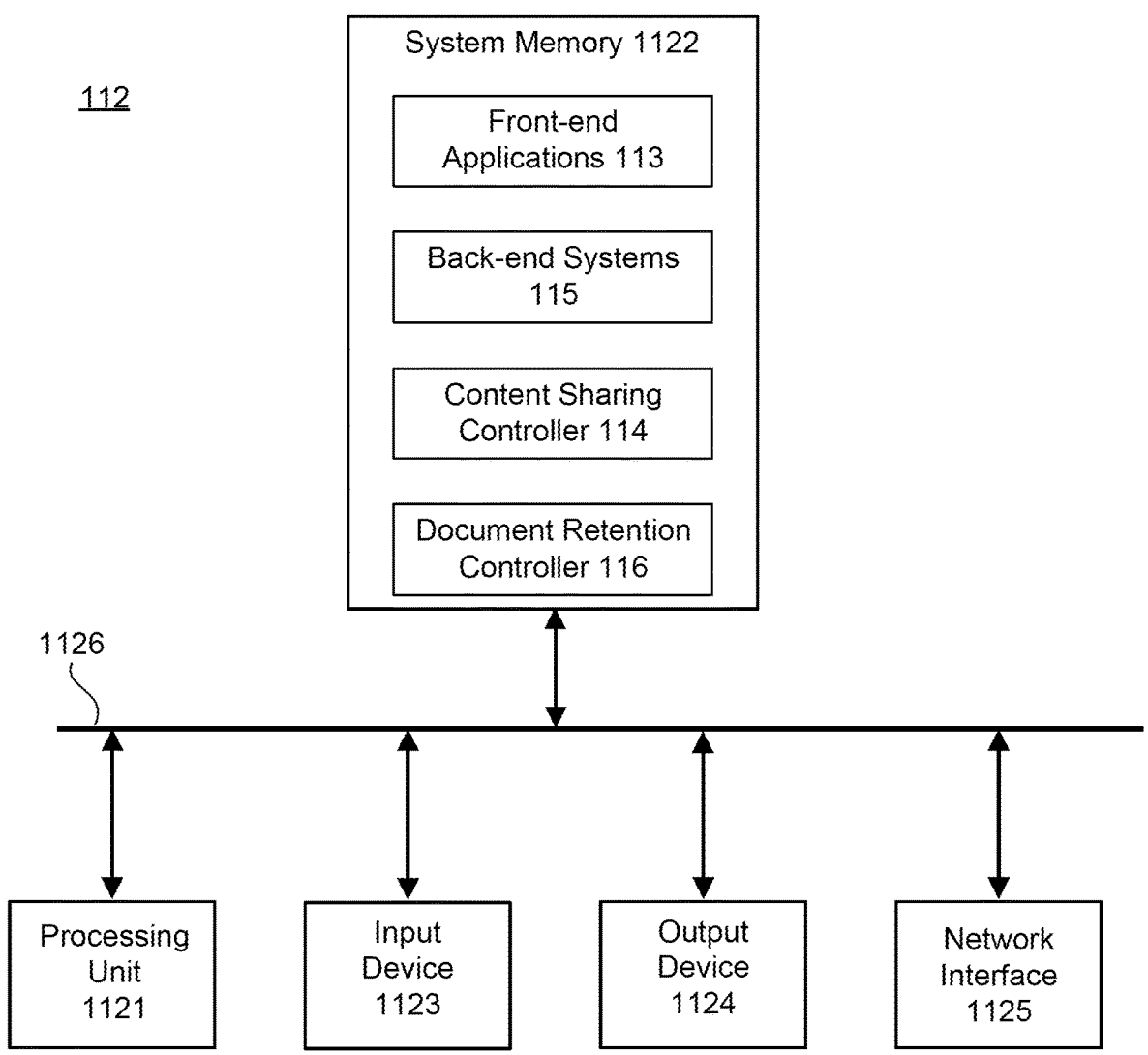
FIG. 5 illustrates an example high level block diagram of the content management server according to one embodiment of the present invention.

FIG. 5 illustrates an example high level block diagram of the content management server 112 according to one embodiment of the present invention. The content management server 112 may be implemented by the computing device 300, and may have a processing unit 1121, a system memory 1122, an input device 1123, an output device 1124, and a network interface 1125, coupled to each other via a system bus 1126. The system memory 1122 may store the front-end applications 113, the back-end systems 115, the content sharing controller 114, and the content retaining controller 116.

A source document 150 may be generated in the specific business context of the first front-end application (e.g., the Research & Development front-end application 208) and stored in the content repository associated with the first front-end application (e.g., the content repository 111*a*). The user may want to use the source document 150 in the specific business context of the second front-end application (e.g., the marketing and sales application 216). Instead of downloading the source document 150 from the content repository 111*a* and then uploading it to the content repository 111*b* associated with the second front-end application, the user may use the content management system 110 to generate a link document 150L in the second content repository 111*b*. The link document 150L may be a copy of the source document 150, linked to it and synchronized with it. The content sharing controller 114 may control the process for generating the link document 150L, and the process for synchronizing the source document 150 and its link document 150L.

Figure 6:
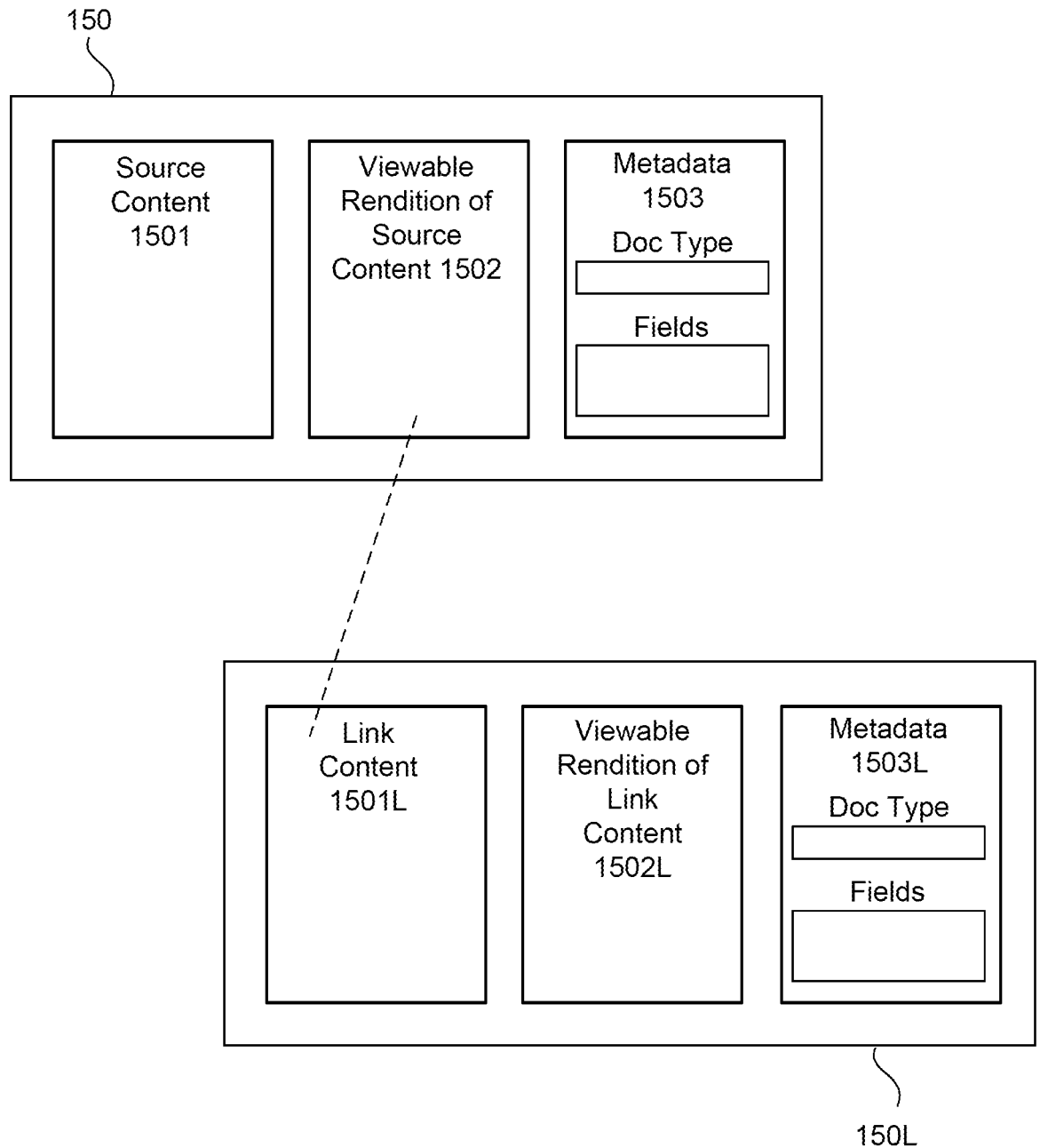
FIG. 6 illustrates an example source document and its link document according to one embodiment of the present invention.

FIG. 6 illustrates an example source document 150 and its link document 150L according to one embodiment of the present invention. As shown, the source document 150 may include the following elements in the source content repository 111*a*: source content 1501 previously uploaded (e.g., a Word document), its viewable rendition 1502 generated by the content management server 112 (e.g., a PDF of the source content 1501), and a set of metadata (fields) 1503. The metadata 1503 may vary by document type (e.g., those described above with reference to FIG. 2 above), and may include document type and fields such as version, date and time it was uploaded, and its lifecycle information. The source document may be in any format.

The link document 150L may include the following elements in the link content repository 111*e*: link content 1501L synchronized with the source document 150 (e.g., the viewable rendition 1502 of the source content), a viewable rendition 1502L of the link content 1501L, and a set of metadata (fields) 1503L of the link document. The metadata 1503L of the link document may vary by document type, and is independent of the source document's metadata. However, a small set of "source document fields" may be synchronized from the source document 150 to provide context to the user. In one implementation, if field names match between the source document 150 and the link document 150L, field values may be defaulted from the source document 150 when the link document 150L is generated. The matched fields may include, e.g., source content repository name, source content repository ID, source document name, source document ID, source document version, latest source document version, and source document owner. The metadata 1503L may include some fields unique to the link document, e.g., a "Link" Boolean (Yes/No) field identifying the link document, and a "Link Status" field indicating if the link is active, deleted or obsolete. The metadata 1503L may also include a link document version number, which is independent of source document version number.

Figure 7A:
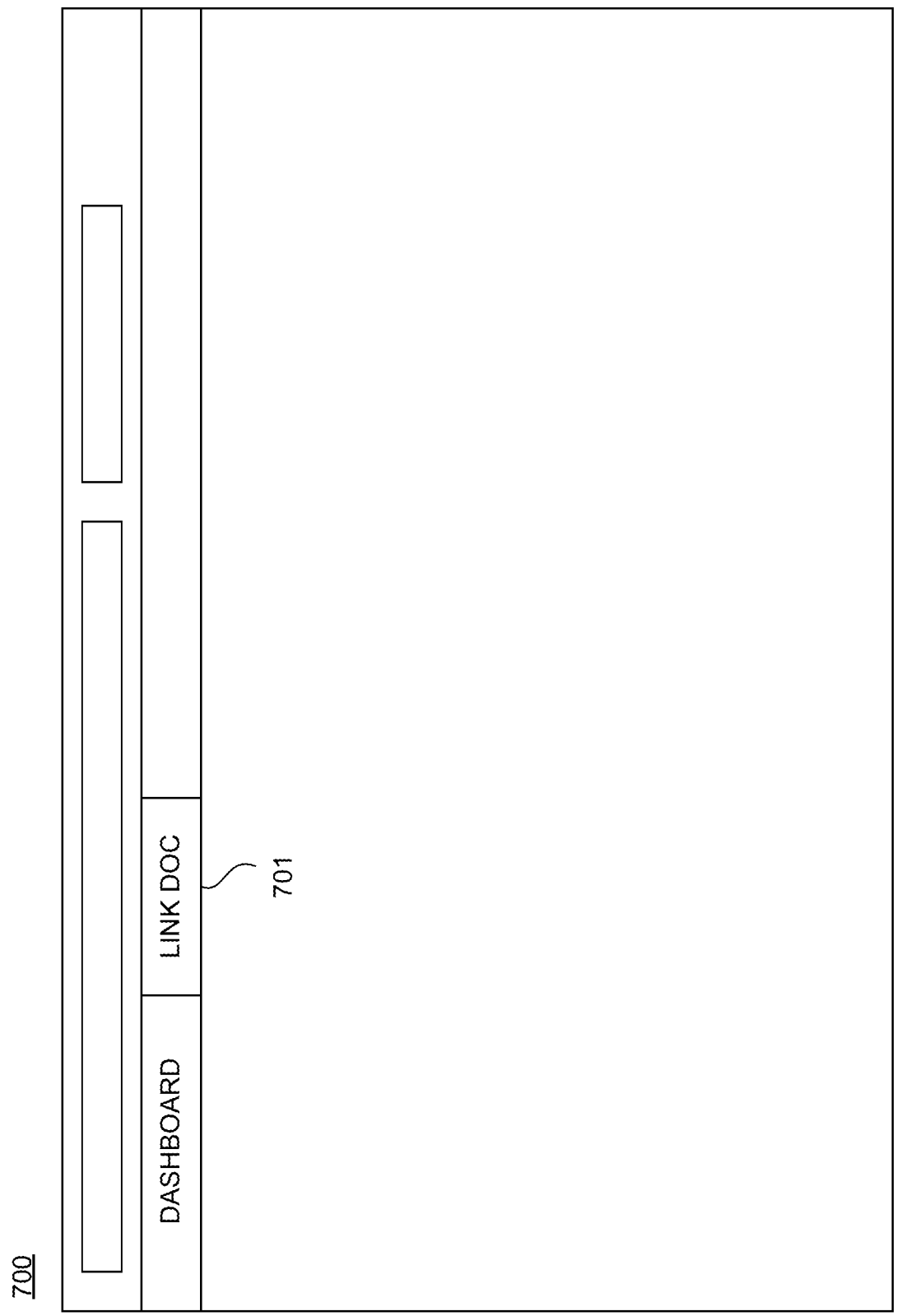
FIGS. 7A and 7B illustrate example UIs for requesting a link document according to one embodiment of the present invention.
Figure 7B:
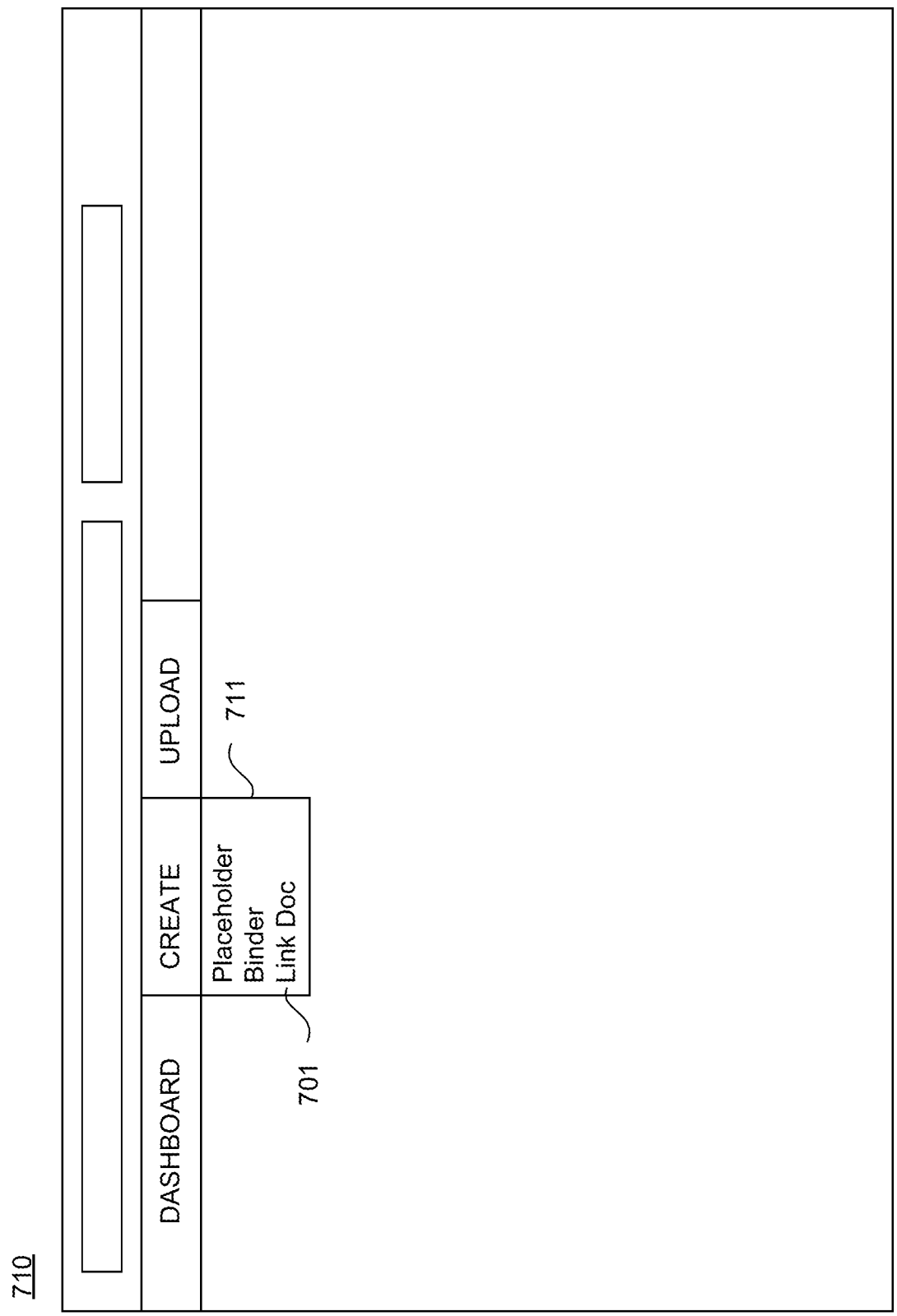

The content management system 110 may allow the user to create the link document 150L in a number of different ways. Generally, a "Link Document" button may be displayed as an option whenever the user wants to create, open or add a document. For example, the "Link Document" button 701 may be provided on the UI 700 of the content management system 110, as shown in FIG. 7A. Alternatively, the "Link Document" button 701 may be provided in a pull down menu 711 on the UI 710 of the content management system 110, as shown in FIG. 7B. The "Link Document" button 701 may also be provided on a UI of a front-end application. The UI 700, UI 710 and UIs to be described below could be a graphical user interface ("GUI") or an application programming interface ("API").

Figure 8:
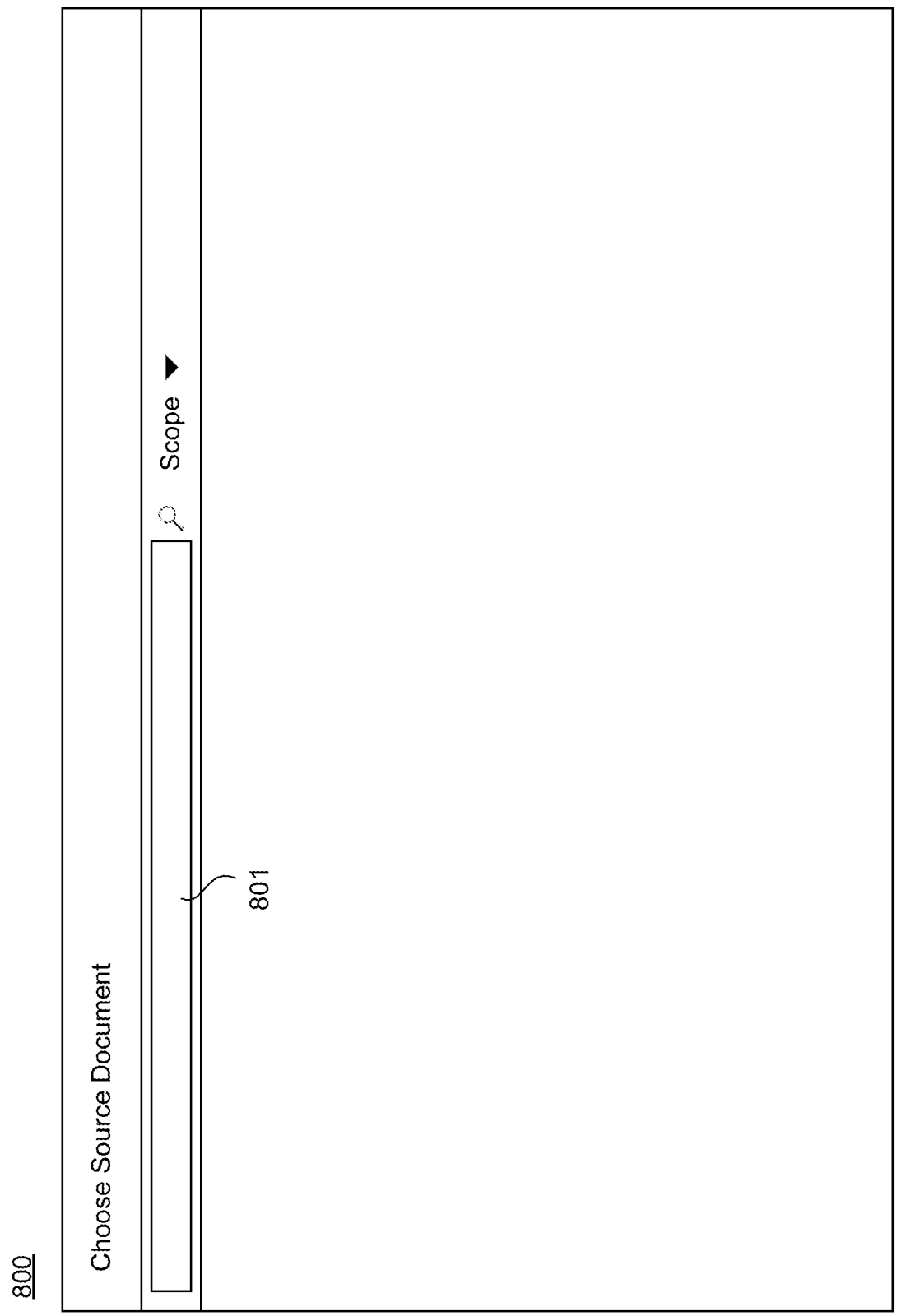
FIG. 8 illustrates an example UI for generating a link document according to one embodiment of the present invention.

When a user clicks on the "Link Document" button 701, a source document selection UI 800 may be displayed, so that the user may search for the source document he can access in the window 801, as shown in FIG. 8. Alternatively, content repositories the user can access may be displayed to allow the user to select the source content repository and the source document.

Figure 9:
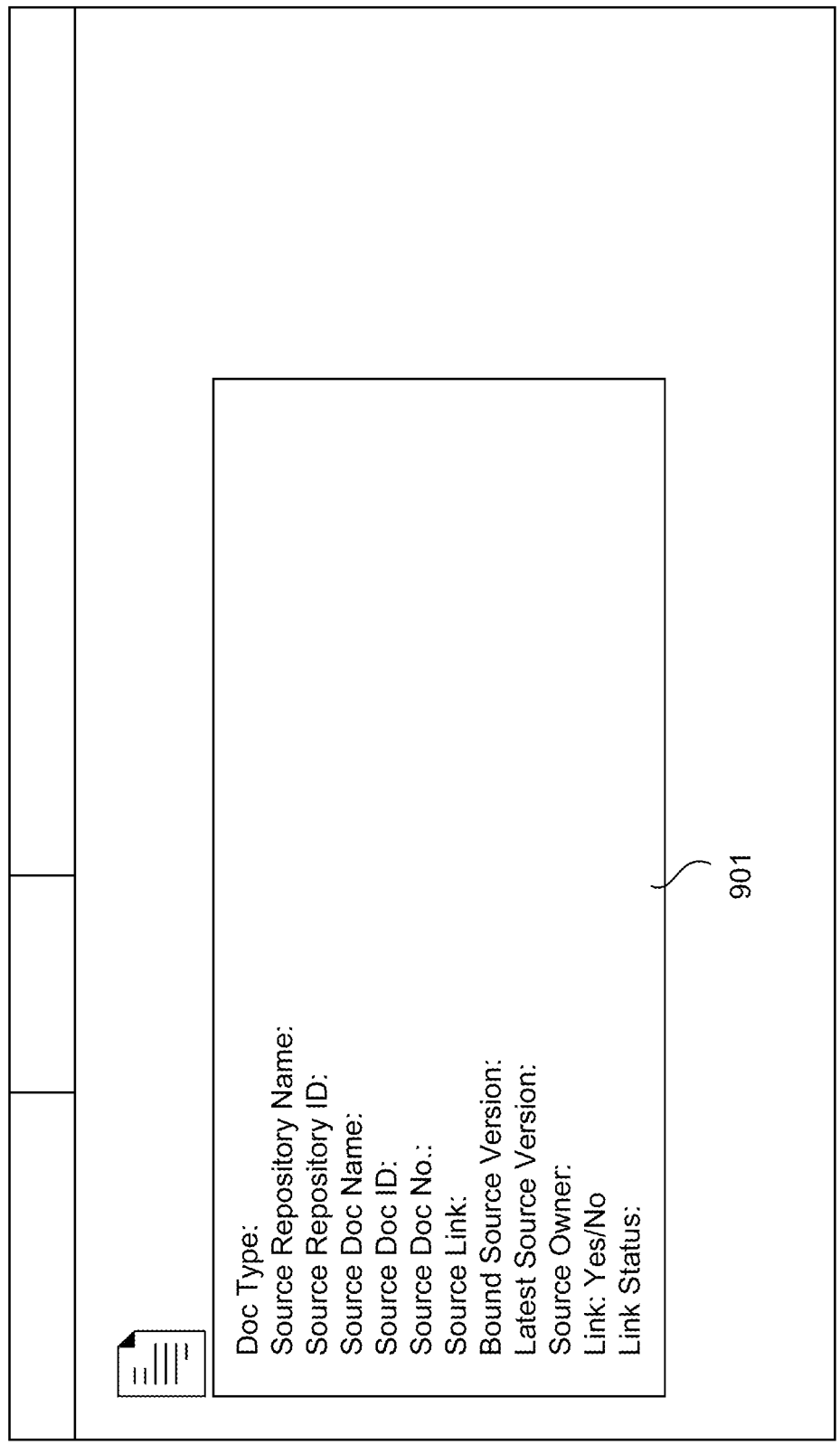
FIG. 9 illustrates an example UI for generating a link document according to one embodiment of the present invention.

When the user selects a source document to create a link document, a link document creation UI may be displayed. As shown in FIG. 9, the link document creation UI may include an area 901 for the user to input metadata 1503L of the link document.

Figure 10A:
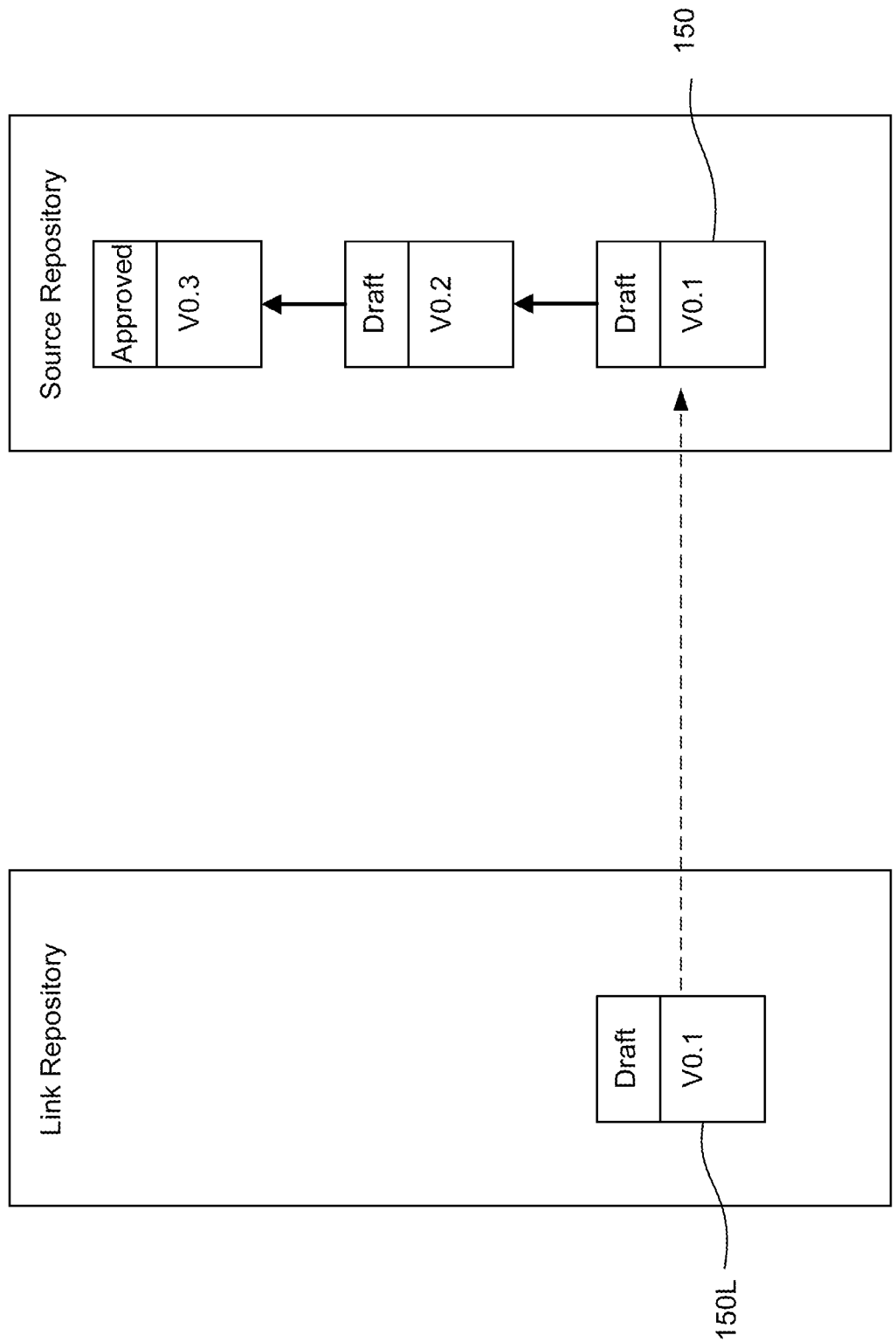
FIGS. 10A-10F illustrate synchronization between a source document and a link document according to one embodiment of the present invention.
Figure 10B:
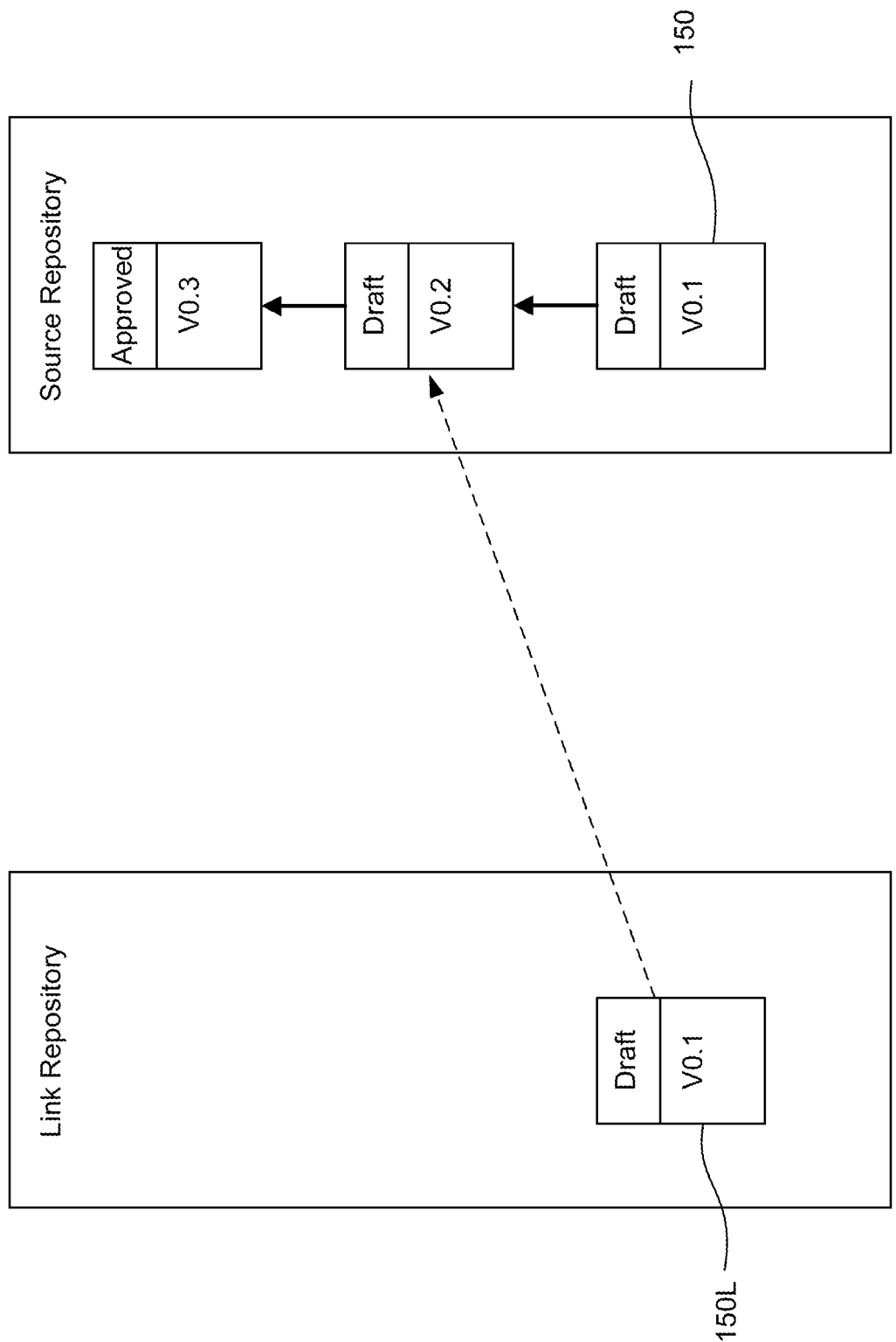
Figure 10C:
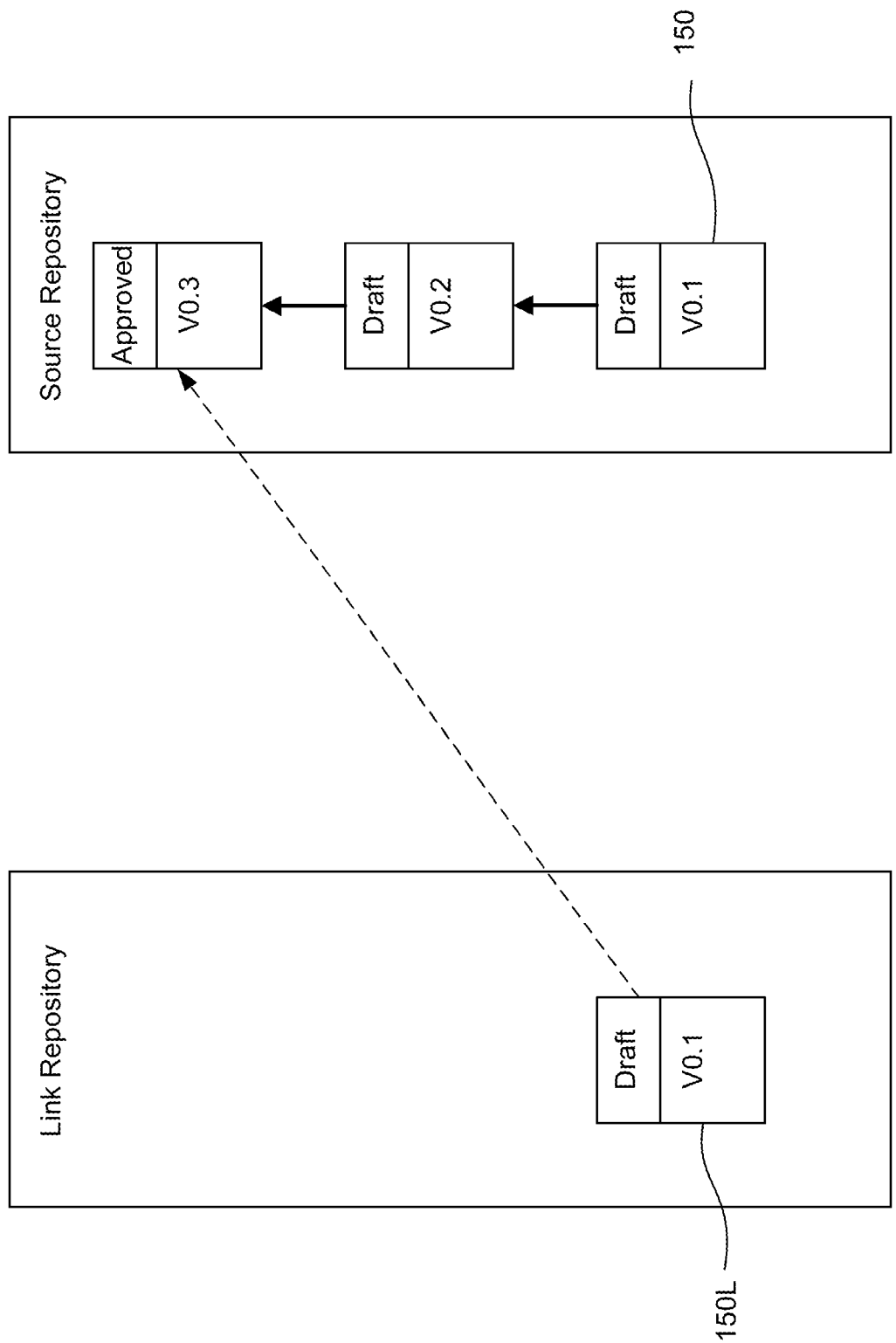

The content management system 110 may also allow the user to choose how the link document 150L and the source document 150 are bound, or synchronized. In one implementation, the link document 150L may be dynamically synchronized to the latest version of the source document 150, and may be updated when the source document 150 is updated and/or changes state. As shown in FIGS. 10A, 10B and 10C, when the source document 150 in the source repository is updated from version 0.1 to version 0.2, the link document 150L in the link repository may be updated with the changes, and when the source document 150 is updated from version 0.2 to version 0.3, the link document 150L may be updated with the changes as well, with the process to be described in detail below with FIG. 11. The link document's version number may be kept independent from the source document's version number, and will change only when the user saves a new version of the link document.

Figure 10D:
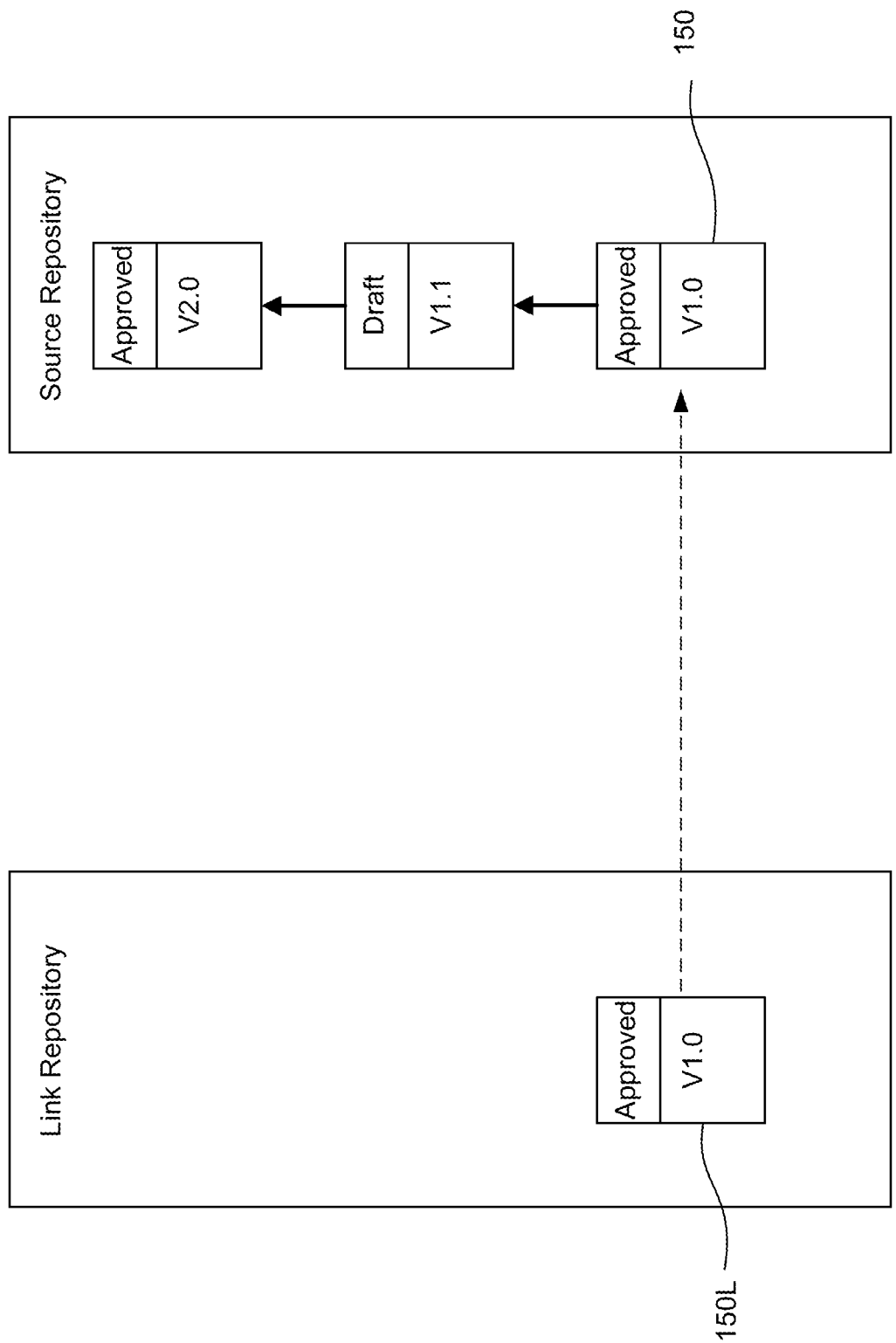
Figure 10E:
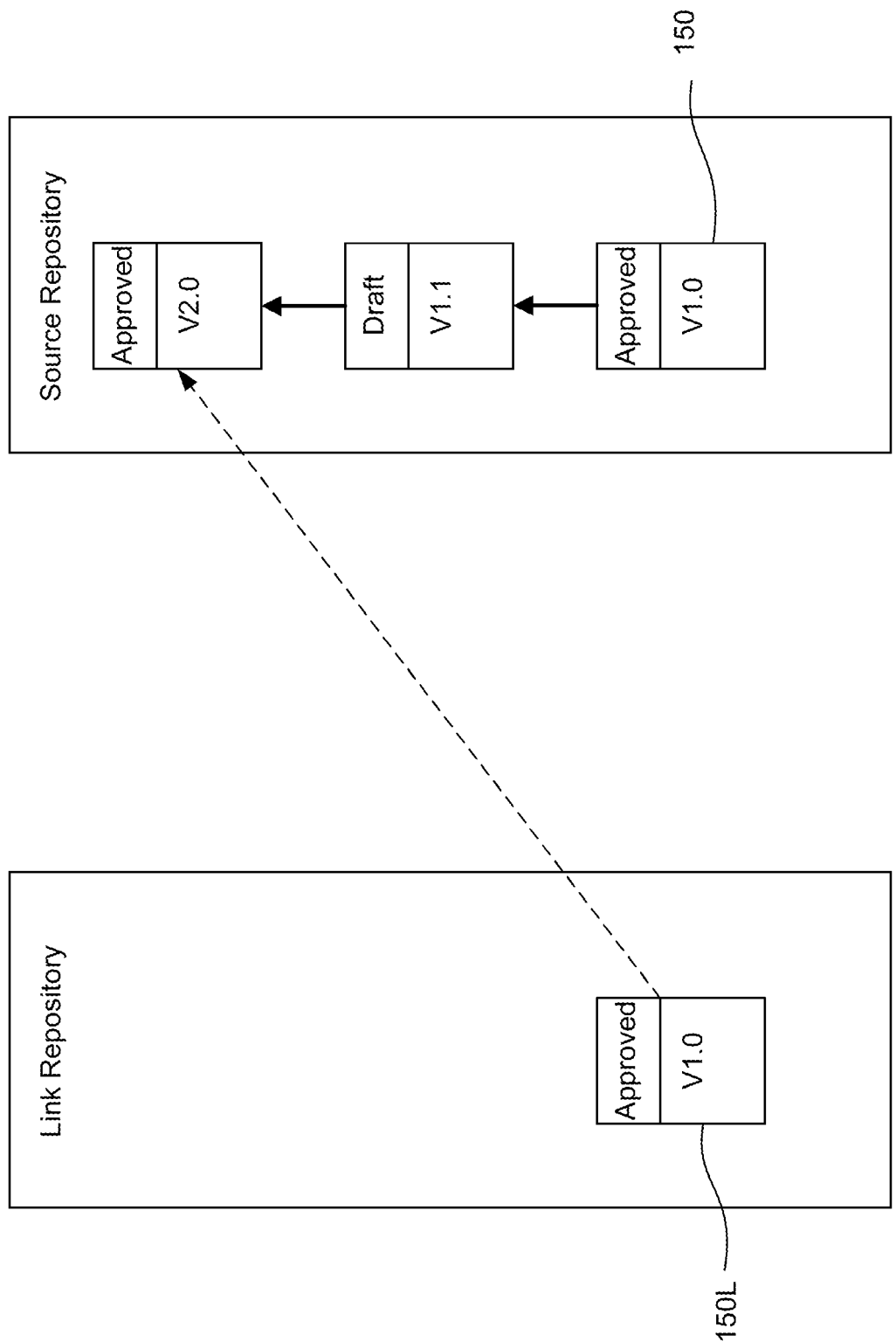

In one implementation, the link document 150L may be dynamically synchronized to the latest steady state version of the source document 150 (e.g., the approved version), so that it is updated only when a new steady state version of the source document is available. As shown in FIGS. 10D and 10E, when the source document 150 in the source repository is updated from an approved version 1.0 to a draft version 1.1, the link document 150L in the link repository may not be updated, since the new version is a draft, not a new steady state version. However, when the source document 150 is updated from version 1.1 to a new approved version 2.0, the link document 150L in the link repository may be updated with the changes, with the process to be described in detail below with FIG. 11.

Figure 10F:
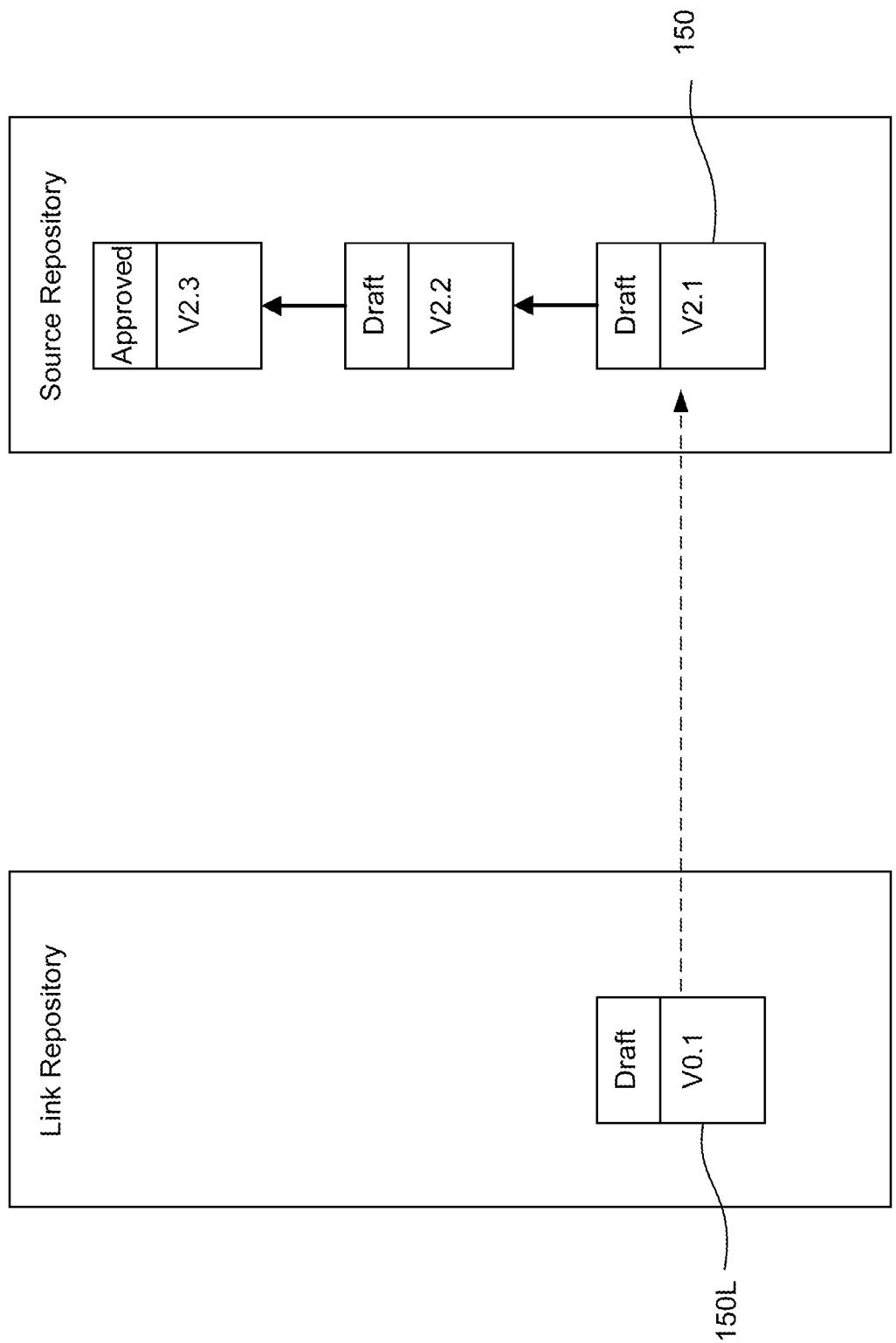

In one implementation, the link document 150L may be statically synchronized to a specific version of the source document 150, and may not be updated even when the source document 150 is updated. As shown in FIG. 10F, when the source document 150 is updated from version 2.1 to 2.2, the link document 150L may be still synchronized to version 2.1, instead of being updated to synchronize with version 2.2.

Certain changes in the source document 150 may trigger updates to the link document 150L, depending on the type of the synchronization. For example, when the link document 150L is synchronized to the latest version of the source document 150, the trigger events may be source document changes, e.g., when a new version of the source document is checked in, a new version is uploaded to the source repository, or a new draft is created. When the link document 150L is synchronized to the viewable rendition 1502 of the source document 150, the trigger events may be rendition changes, e.g., re-rendering actions, uploading or replacing the viewable rendition, deleting the viewable rendition, changing the signature page definition, adding a signature, or changing the overlay applied to the source document. When the link document 150L is synchronized to the steady state version of the source document 150, the trigger events may be state change to the steady state. In addition, field change of one of the "Source Document Fields" of the link document 150L may trigger changes to these fields, and source document deletion may trigger field change of the link document 150L as well.

Actions on the source document 150 may not be restricted simply because it has a link document 150L. A request to delete the source document 150 may be allowed, but a notice that it has a link document 150L may be displayed before the deletion.

Link documents may have their own lifecycle independent of the source document lifecycle, and link actions may be controlled by their lifecycle. There may be restrictions on link actions, e.g., copying, checking out, checking in, uploading new version, managing renditions and other content-related actions. Other types of restrictions may include allowing draft creating for increment versions only, and allowing annotating for specific version synchronization only.

Ability to create a link document may be controlled by a User Profile permission, which may be defaulted on for system administrator and repository owner. When a user creates a link document, the potential source documents are limited to those he has permission to view in the source repository. Access to content and fields of the link document 150L may be determined by the link document's sharing settings, independent of the source document access.

Figure 11:
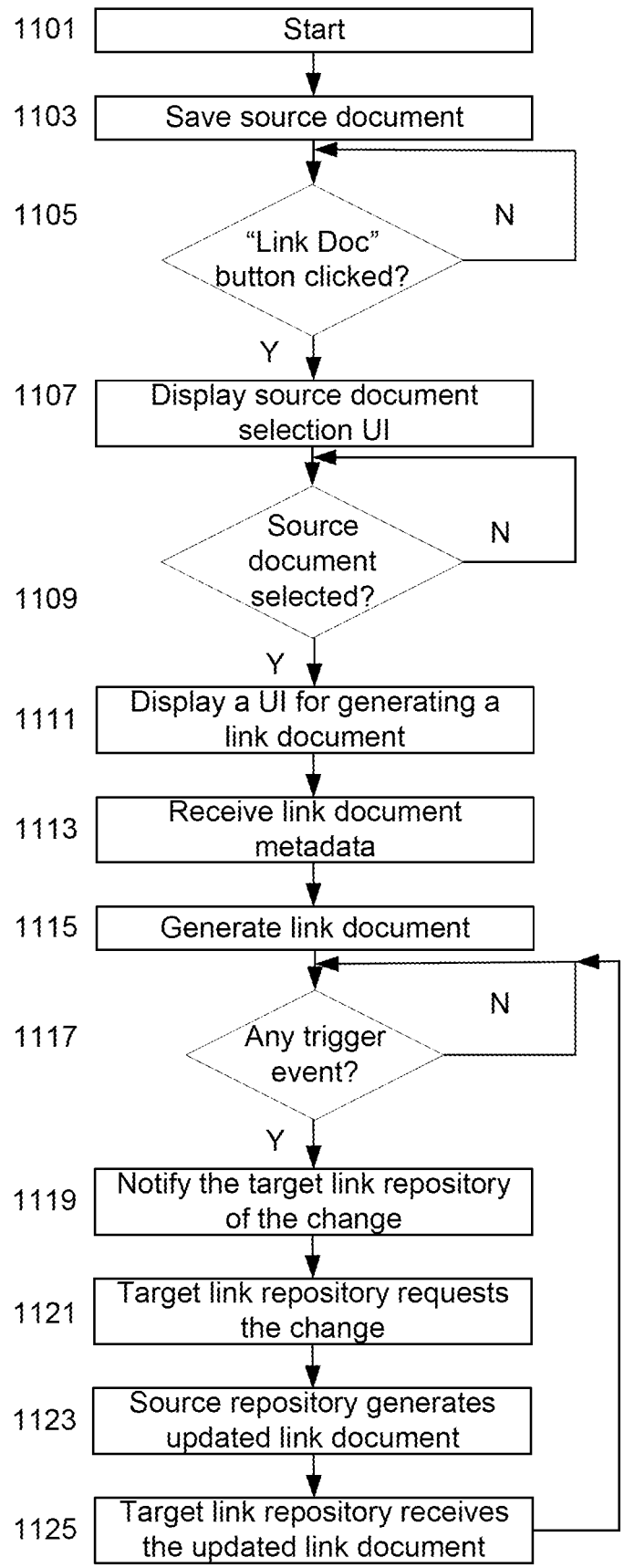
FIG. 11 illustrates a flowchart of a method for sharing content across repositories in an enterprise content management system according to one embodiment of the present invention.

FIG. 11 illustrates a flowchart of a method for re-using content across repositories in the enterprise content management system 100 (as shown in FIG. 1) according to one embodiment of the present invention.

The process may start at 1101.

At 1103, a first user may save a source document 150 in a content repository (e.g., the content repository 111a) with a user computing device (e.g., the user computing device 120a). The source document 150 may be saved with the Research & Development (R&D) front-end application 208 according to its specific business process for supporting research and initial clinical trial submissions. The source document 150 may include the source content 1501 (e.g., a Word document) uploaded by the user, its viewable rendition 1502 (e.g., a PDF of the source content) generated by the content management server 112, and a set of metadata (fields) 1503 of the source document, as shown in FIG. 6.

A second user may want to use the source document 150 with the business process of a second front-end application (e.g., the marketing and sales application 216). Instead of downloading the source document 150 from the content repository 111a associated with the first front-end application and then uploading it to the content repository 111e associated with the second front-end application, the user may use the content management system 110 to create a link document 150L. The content management system 110 may allow the user to create the link document 150L in a number of different ways. As shown in FIGS. 7A, and 7B, a "Link Document" button 701 may be displayed as an option whenever the user wants to create, open or add a document.

At 1105, it may be determined if the "Link Document" button 701 is clicked.

If yes, at 1107, a source document selection UI 800 may be displayed, so that the user may select the source document and its repository, or search for the source document, as shown in FIG. 8.

At 1109, it may be determined if a source document is selected to create a link document.

If yes, at 1111, a link document creation UI may be displayed. As shown in FIG. 9, the link document creation UI 900 may include an area 901 for the user to input metadata 1503L of the link document 150L. The link document 150L may have its own set of metadata (fields) that varies by document type, and is independent of the source document's metadata. In one implementation, a small set of source document fields may be defaulted from the source document 150 to provide context to the user.

One field of the metadata 1503L may be used to allow the user to select the type of synchronization between the link document 150L and the source document 150, e.g., on the link document creation UI 900. As described above, the link document 150L may be dynamically synchronized with the latest version of the source document 150, dynamically synchronized with a steady state version of the source document 150, or statically synchronized with a specific version of the source document 150. In one implementation, the link content 1501L may be synchronized with the viewable rendition 1502 of the source document 150. In one implementation, the link content 1501L may be synchronized with the source content 1501 of the source document 150.

One field of the metadata 1503L may be used to allow the user to add an overlay (e.g., "Draft" or "Confidential") or signature to the link content 1501L and/or its viewable rendition 1502L.

At 1113, metadata 1503L of the link document 150L may be received.

When the user finishes inputting metadata 1503L of the link document 150L, at 1115, the link document 150L may be generated by the content management system 110 and stored in the link repository 111e. As shown in FIG. 6, the link document may include the link content 1501L, the viewable rendition 1502L of the link content 1501L, and metadata 1503L.

At 1117, it may be determined if there is a trigger event for updating the link document 150L. The trigger event may depend on the type of synchronization between the source document 150 and the link document 150L.

If yes, at 1119, a message may be sent to the target link repository 111e from the source content repository 111a to notify the target link repository 111e of the change to the source document information or to the source document's viewable rendition.

The system may be overloaded when there are multiple repositories, each has one or more source documents, and each source document has one or more link documents in other repositories. In one implementation, a queueing system may be used to prevent overloading. When there is a trigger event to a source document in one repository, instead of sending the updates to target link repositories, the source repository may use an outbound queue to queue the messages to target link repositories. In one implementation, the queue is durable and the queue contents would be preserved if the system were to crash suddenly. After the system recovers, it can continue processing where it was left off. Specifically, for each trigger event, the message may include the ID of the source repository, the ID of the source document involved, the version of the source document, the trigger event, the target link document ID, the target link repository ID, and the nature of the change (e.g., a new version, or a change in the viewable rendition).

Each link repository may use an inbound queue to receive messages from its source repositories, and a message may be added to its inbound queue only if it is a target link repository in the message. For each trigger event in its inbound queue, the target link repository may locate the target link document, check the metadata 1503L of the target link document, and determine if the target link document should be updated. If yes, at 1121, the target link repository 111e may send a pull request to the source repository 111a for the change.

At 1123, an updated link document may be generated at the source repository 111a.

At 1125, the updated link document may be received by the link repository 111e from the source repository 111a. The link repository 111e may then move to the next message in its inbound queue.

Alternatively, the updates may be pushed to the target link repository from the source repository.

At the source repository, the process may return to 1117.

In the content manage system of the present invention, the source document is kept in the source repository, and only its link document is re-used in the link repository. The source document may keep a list of its dependent link documents and link repository. Although the source repository and the link repository have different business contexts, the re-use of the link document in the link repository does not directly impact the source document's content, and users of the link document can't make changes to the source document. Thus, the source document may be kept as the single source of truth, while the link documents may be kept synchronized with the source document according to the type of synchronization selected by the user.

In practice, a link document in a second repository may need to be archived at a certain point in its life cycle for business or compliance purposes, and changes to it are not permitted after that point. The present invention provides a method for keeping the archived version of the link document from being affected by operations on the link document, the source document or other related documents, such as updates and deletion, so that these documents can continue to be active. FIG. 12 illustrates a flowchart of a method for retaining a static copy of a link document in an enterprise content management system according to one embodiment of the present invention. The process may be controlled by the content retaining controller 116 shown in FIG. 1, and start at 1201.

At 1203, one or more predetermined requirements for retaining a static copy of a link document (e.g., the link document 150L), or a reused document, may be received, e.g., at the content retaining controller 116. The predetermined requirements may include, e.g., when a document in a clinical trial system is archived, or when a user request for archiving the link document is received.

At 1204, it may be determined, e.g., by the content retaining controller 116, if there is a link document in documents to be archived. A document is determined as a link document when its cross-link field indicates that is a link document.

If yes, at 1205, it may be determined, e.g., by the content retaining controller 116, if a predetermined requirement for retaining a static copy of the link document is met.

If yes, a static copy of the link document may be created at 1207. When the predetermined requirement is when a document in a clinical trial system is archived, the process for creating the static copy may be initiated at the same time that the archiving process is initiated. The static copy of the link document is not cross-linked to any other documents, and is a database level copy of the link document which comprises all information in the content management related to the link document, e.g., metadata, Document Number, Document ID, the source document, relationships with the source document and other documents cross-linked to the link document, sharing setting, the audit trail, all relevant versions of the link document and other attachments.

The process for creating the static copy may include distinguishing which versions in the version tree of the link document are relevant, pulling them over, and copying all of the relevant versions. The process may include exporting the audit trail from the link document, and make it available as a standard rendition on the static copy of the link document, so that the audit trail does not need to be sourced from the link document, and users can open the rendition on the static copy and read it there. The process may include creating a relationship to the link document. The relationships are real relationships on the static copy in the way the relationships look on the link document, so that users can review in the relationship section of the metadata or the document information on the static copy. The process may include recreating renditions of the link document, and the renditions are recreated as real renditions as well and are part of the static copy. The process may also include recreating attachments and the sharing settings.

The creation of the static copy of the link document does not affect the link document, which is still stored in the content management system 111, the cross link is still active, and the link document can still be reused in future. In one embodiment, the source document is in one repository (e.g., 111a), the link document is in a second repository (e.g., 111b), and the static copy of the crosslinked document could be in the first repository, the second repository, or a third repository (e.g., 111c). If the source document is deleted, the static copy can still be used as normal.

At 1209, the completed clinical trial study may be removed from the link document when its documents are archived and a static copy of the documents are created and stored. The link document can still be active and reused, while the static copy of the documents is protected from changes to be compliant with the regulatory requirements.

An electronic trial master file ("eTMF") is used to manage clinical documents across the life cycle of a clinical trial.

The eTMF systems are required to maintain compliance with the regulatory agencies as well as present a historical look at the actions that have been taken over the course of a clinical trial. When a clinical trial study is completed and documents are ready to be stored and basically lockdown, the documents need to be archived with no further changes to meet the regulatory requirements. However, documents in the completed study may be linked to documents in other studies, or reused in or associated to other studies, and may need to be updated for the active studies. To be compliant with the regulatory requirements, users have to identify documents to be put into the archive for the archived study that can no longer be edited verses the documents which can continue to be associated with active studies and continue to be reused and modified. If there are documents associated with other studies and need to be reused, a single study copy needs to be archived and protected from further changes. At the same time, the completed study which has been archived needs to be removed from the documents which will be reused and edited. The process shown in FIG. 12 may be used to make the process more accurate and efficient.

In one embodiment, when it is time to archive documents of a study, a user request to initiate the study archival may be received.

In response, the content management server 112 may automatically go through all the archival steps, and at the same time create a static copy of documents archived. Among all of the documents associated with archived study, the content retaining controller 116 may determine which ones have multiple studies in the study field of the documents, and create a static copy of each of them.

In one embodiment, the content retaining controller 116 may identify completed study that is archived into the study field on that document, and remove the completed study from the link document. Consequently, the link document may continue to stay live, be active for other studies, and is no longer associated with the completed study that is archived, while the completed study that has been archived has its own static copy of that document which can not be modified again.

The above-described features and applications can be implemented as software processes that are specified as a set of instructions recorded on a computer readable storage medium (also referred to as computer readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

In this specification, the term "software" is meant to include firmware residing in read-only memory or applications stored in magnetic storage, which can be read into memory for processing by a processor. Also, in some implementations, multiple software technologies can be implemented as sub-parts of a larger program while remaining distinct software technologies. In some implementations, multiple software technologies can also be implemented as separate programs. Finally, any combination of separate programs that together implement a software technology described here is within the scope of the subject technology. In some implementations, the software programs, when installed to operate on one or more electronic systems, define one or more specific machine implementations that execute and perform the operations of the software programs. Examples of computer programs or computer code include machine code, for example is produced by a compiler, and files including higher-level code that are executed by a computer, an electronic component, or a microprocessor using an interpreter.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

It is understood that any specific order or hierarchy of steps in the processes disclosed is an illustration of example approaches. Based upon design preferences, it is understood that the specific order or hierarchy of steps in the processes may be rearranged, or that all illustrated steps be performed. Some of the steps may be performed simultaneously. For example, in certain circumstances, multitasking and parallel processing may be advantageous. Moreover, the separation of various system components illustrated above should not be understood as requiring such separation, and it should be understood that the described program components and systems can generally be integrated together in a single software product or packaged into multiple software products.

Various modifications to these aspects will be readily apparent, and the generic principles defined herein may be applied to other aspects. Thus, the claims are not intended to be limited to the aspects shown herein, but is to be accorded the full scope consistent with the language claims, where reference to an element in the singular is not intended to mean "one and only one" unless specifically so stated, but rather "one or more." Unless specifically stated otherwise, the term "some" refers to one or more.

What is claimed is:

1. A computer-implemented method for retaining content in a content management system, wherein the content management system comprises a first repository and a second repository, the method comprising:
storing a source document in the first repository;
receiving a request for generating a link document in the second repository;
displaying a user interface ("UI") for selecting a source document in response to the request for generating the link document;
displaying a UI for generating the link document;
receiving link document metadata on the UI for generating the link document, wherein the link document metadata comprises a first field for indicating a type of synchronization between the link document and the source document;
generating the link document comprising metadata and a document identifier in the second repository, wherein the link document is a copy of the source document and is synchronized to the source document;
receiving a first predetermined requirement for creating a static copy of the link document; and
creating a static copy of the link document when the first predetermined requirement is satisfied, wherein no change is permitted to be made to the static copy of the link document, wherein the static copy of the link document is a database level copy of the link document such that the static copy of the link document includes the metadata and the document identifier of the link document, and wherein the static copy of the link document is independent of the link document such that:
in response to deleting the link document, the static copy of the link document is available for access.

2. The method of claim 1, wherein the first repository is associated with a process of a first front-end application, and the second repository is associated with a process of a second front-end application.

3. The method of claim 1, wherein the static copy of the link document is a database level copy of the link document such that the static copy of the link document comprises all information in the content management system related to the link document.

4. The method of claim 1, wherein the static copy of the link document comprises a copy of the source document.

5. The method of claim 1, wherein the static copy of the link document comprises a relationship between the link document and the source document.

6. The method of claim 1, wherein the static copy of the link document comprises a relationship between the link document and a second document linked to the link document.

7. The method of claim 1, wherein the static copy of the link document comprises a relationship between the link document and the static copy of the link document.

8. The method of claim 1, wherein the static copy of the link document comprises sharing setting information of the link document.

9. The method of claim 1, wherein the static copy of the link document comprises a second rendition of the link document.

10. The method of claim 1, wherein the static copy of the link document comprises an attachment of the link document.

11. The method of claim 1, wherein the static copy of the link document is not linked to any other documents in the content management system.

12. The method of claim 11, further comprising: determining, by a content retaining controller, if the first predetermined requirement is satisfied.

13. The method of claim 12, further comprising: determining that a second version of the link document is relevant and including the second version of the link document into the static copy of the link document.

14. The method of claim 1, further comprising: exporting an audit trail from the link document, and including the audit trail as a standard rendition into the static copy of the link document.

15. The method of claim 1, wherein the predetermined requirement is a user request for creating a static copy of the link document.

16. The method of claim 1, wherein the predetermined requirement is archiving the link document.

17. The method of claim 16, wherein the link document is for a completed clinical study trial in an electronic trial master file ("eTMF") system.

* * * * *